US009717950B2

(12) United States Patent
Sigal et al.

(10) Patent No.: US 9,717,950 B2
(45) Date of Patent: Aug. 1, 2017

(54) GAMIFIED EXERCISE APPARATUS, SYSTEM AND METHOD

(71) Applicant: TOME, INC., Ferndale, MI (US)

(72) Inventors: Jacob R. Sigal, Ferndale, MI (US); Massimo Baldini, Beverly Hills, MI (US)

(73) Assignee: TOME, INC., Ferndale, MI (US)

( * ) Notice: Subject to any disclaimer, the term of this patent is extended or adjusted under 35 U.S.C. 154(b) by 147 days.

(21) Appl. No.: 14/748,998

(22) Filed: Jun. 24, 2015

(65) Prior Publication Data

US 2015/0375040 A1 Dec. 31, 2015

Related U.S. Application Data

(60) Provisional application No. 62/017,533, filed on Jun. 26, 2014.

(51) Int. Cl.
*A63B 24/00* (2006.01)
*G03G 15/00* (2006.01)
(Continued)

(52) U.S. Cl.
CPC ...... *A63B 24/0059* (2013.01); *A63B 71/0622* (2013.01); *G03G 15/5083* (2013.01); *G06F 19/3481* (2013.01); *G06Q 10/02* (2013.01); *G06Q 10/0639* (2013.01); *G06Q 30/00* (2013.01); *A47B 2220/06* (2013.01); *A63B 22/02* (2013.01); *A63B 22/04* (2013.01);
(Continued)

(58) Field of Classification Search
CPC . A63B 24/0059; A63B 24/0087; A63B 22/02; A63B 22/0605; A63B 22/04; A63B 71/0616; A63B 71/0622; A63B 2225/20; A63B 2225/50; G06Q 30/00; G06Q 10/02; G06Q 10/0639
USPC ........................................................ 482/1–9
See application file for complete search history.

(56) References Cited

U.S. PATENT DOCUMENTS 5,813,947 A 9/1998 Densmore
7,614,991 B2 11/2009 Fox
(Continued)

FOREIGN PATENT DOCUMENTS

WO 2008030366 A2 3/2008

*Primary Examiner* — Glenn Richman
(74) *Attorney, Agent, or Firm* — Stephen T. Olson; Harness, Dickey & Pierce, P.L.C.

(57) ABSTRACT

The present system relates to an exercise system comprising an appliance which acts much like an exercise device able, which is able to be used by an individual to enable repeated movements of one or more limbs, to thus enable the user to achieve a low level aerobic activity (e.g., low level exercise) while performing other non-exercise related tasks. A communication control module communicates with a personal electronic device located at the exercise device. A management subsystem communicates with the communication control module and is configured to track usage of the exercise device by at least one individual, and to implement at least one gamification subsystem. The gamification subsystem uses the tracked usage for the purpose of executing a program to reward usage of the exercise device. The gamification subsystem may also be configured to report information it generates to at least one of the individual or an entity associated with operation of the exercise device.

13 Claims, 1 Drawing Sheet

(51) Int. Cl.
  *G06Q 10/06* (2012.01)
  *G06Q 10/02* (2012.01)
  *G06Q 30/00* (2012.01)
  *A63B 22/02* (2006.01)
  *A63B 22/06* (2006.01)
  *A63B 71/06* (2006.01)
  *A63B 22/04* (2006.01)
  *G06F 19/00* (2011.01)
  *H04M 1/725* (2006.01)

(52) U.S. Cl.
  CPC ....... *A63B 22/0605* (2013.01); *A63B 24/0087* (2013.01); *A63B 71/0616* (2013.01); *A63B 2225/20* (2013.01); *A63B 2225/50* (2013.01); *G06F 19/328* (2013.01); *H04M 1/72522* (2013.01)

(56) References Cited

U.S. PATENT DOCUMENTS

| | | | |
|---|---|---|---|
| 7,892,148 B1 | 2/2011 | Stauffer et al. | |
| 2002/0082142 A1* | 6/2002 | Cannon | A63B 71/0697 482/1 |
| 2008/0234111 A1 | 9/2008 | Packham | |
| 2012/0179772 A1* | 7/2012 | Hinnebusch | A63B 24/0084 709/213 |

* cited by examiner

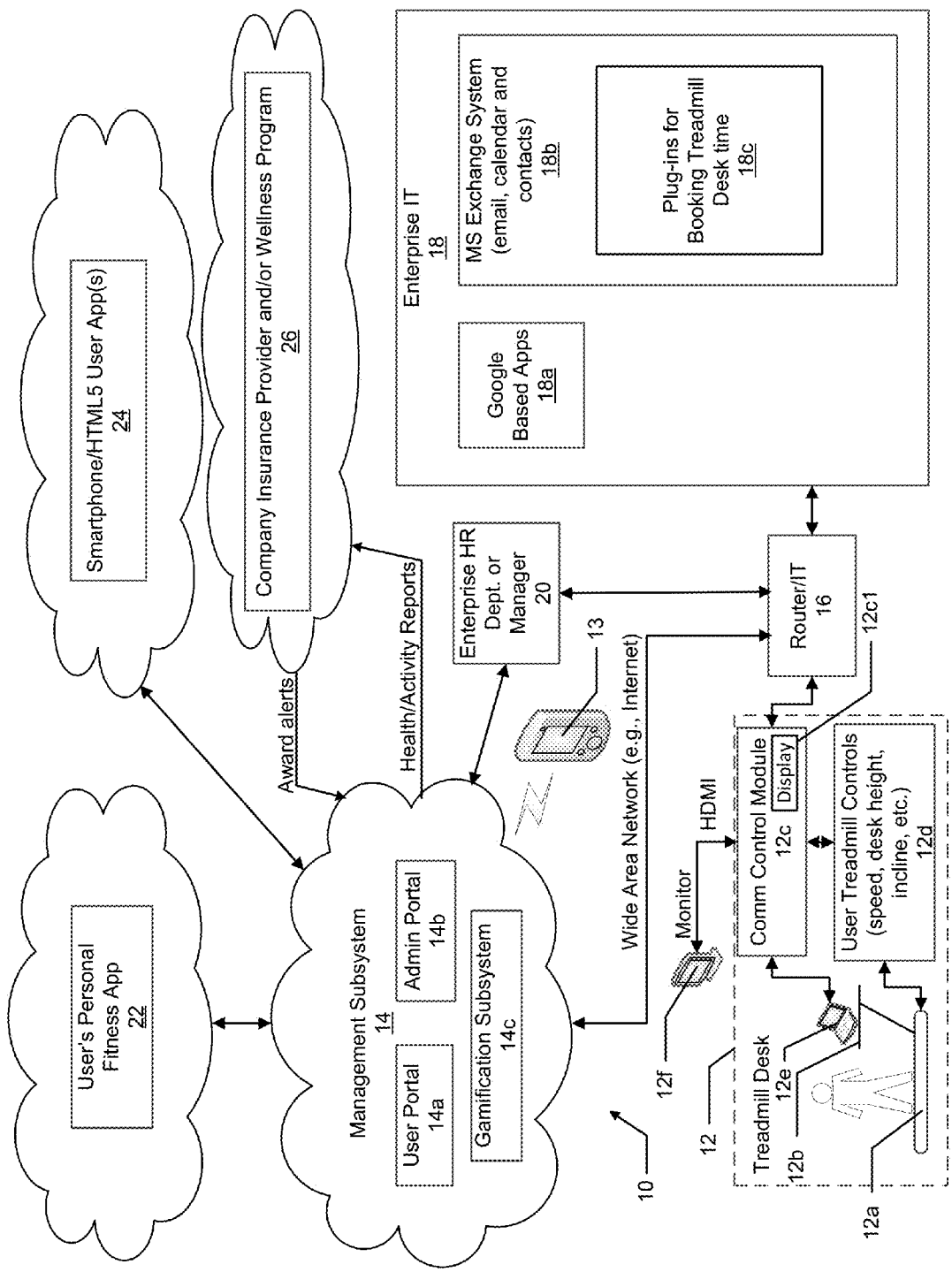

GAMIFIED EXERCISE APPARATUS, SYSTEM AND METHOD

CROSS-REFERENCE TO RELATED APPLICATIONS

This application claims the benefit of U.S. Provisional Application No. 62/017,533, filed on Jun. 26, 2014. The entire disclosure of the above application is incorporated herein by reference.

FIELD

The present disclosure relates to a gamified exercise apparatus and method. In one particular form the apparatus may take the form of a treadmill desk having an associated exercise apparatus such as a treadmill and a user adjustable desk component, as well as an electronic communication subsystem which is able to communicate with a cloud-based subsystem, and where the cloud-based subsystem is able to help encourage use of the desk, to track usage of the desk by employees or workers, and to report on user activity on each one or more of a plurality of treadmill desk components at an enterprise, as well as to facilitate gamification of the work desk to further help encourage use of the desk and resulting well-being of the users.

BACKGROUND

The statements in this section merely provide background information related to the present disclosure and may not constitute prior art.

Interest in health and fitness has increased significantly in the past few years. People are generally more conscious and interested in finding ways to exercise, and especially in activities that are easy to integrate into everyday schedules and routines. Improved cardiovascular health and weight reduction for some individuals can mean more energy available throughout the day, improved attentiveness, improved mood and improved general well-being.

While visits to health clubs before or after work are possible by some individuals, with many other individuals, family commitments, or even work or travel commitments, make it difficult to follow a routine at a health club. Spending time at a health club also takes away from the limited family or free time that individuals have outside of work. An inability to maintain a commitment to a health club often leads to complete abandonment of health objectives.

Many individuals are now involved with desk or office type jobs and occupations where it is common to spend long periods of time seated at a computer terminal or making or fielding number phone calls. Many individuals working in an office environment spend a good part of every work day sitting for long stretches of time in front of a computer or talking on the phone.

Even in a home environment, it is now common to have a home office set up where one can work at home part time, or even full time, performing computer related work such as checking and sending emails, managing calendar appointments, creating reports or spreadsheets, etc., all typically while seated at a conventional desk.

In view of the significant time constraints many individuals face with work and/or family commitments, and the significant time that many individuals find themselves spending at a desk doing computer or telephone related work, it would be a significant time savings if one could integrate low level aerobic activity, for example, walking on a treadmill, with a system that allows full connectivity to the individuals work enterprise while the individual accesses computer related accounts from his/her enterprise (e.g., email, calendar, contacts) or enterprise supplied applications (word processing or spreadsheet applications) while simultaneously getting the health benefits of low level low level aerobic activity projects.

It would further be a significant benefit if the activity of the treadmill could be integrated with some external subsystem, for example a cloud-based subsystem, that could track and report the activity of each user of the treadmill to the user's enterprise (i.e., place of employment) and facilitate gamification of treadmill activities to motivate individuals to make use of the treadmills whenever the opportunity presents itself. Such a system that implements gamification would not only allow an individual to burn calories and obtain the aerobic benefits of walking for short time intervals (e.g., 15 minutes, 30 minutes or longer per interval), all while keeping a record of the individuals participation on the treadmill, but could make such use even more enjoyable by creating and monitoring user activities on the treadmill in a manner that fosters competition among individuals for enterprise supplied prizes and awards. The health benefits to individuals of the enterprise in improved health and well-being may well help to improve productivity of the system.

SUMMARY

In one aspect the present system relates to an exercise system having an appliance which allows repeated movements of one or more limbs of an individual to thus act much like an exercise device which the individual can use to perform a low level aerobic activity while simultaneously performing other non-exercise related tasks. The system also includes a communication control module able to communicate with a personal electronic device located at the exercise device. The system further includes a management subsystem in communication with the communication control module. The management subsystem may be configured to track usage of the exercise device by at least one individual, and to implement at least one gamification subsystem. The gamification subsystem may make use of the tracked usage for the purpose of executing a program to reward usage of the exercise device. The gamification subsystem may also be configured to report information generated by the gamification program to at least one of the individual or an entity associated with operation of the exercise device.

In another aspect the present disclosure relates to an exercise system comprising an appliance that enables repeated movements of one or more limbs of an individual, and thus operates as an exercise device, to thus enable the individual to achieve a low level aerobic activity while simultaneously performing other non-exercise related tasks. The system may also include a control subsystem including user controls for adjusting an operating parameter associated with the exercise device. A communication control module may be included which is able to communicate with personal electronic devices of different users, where the personal electronic devices are located at the exercise device. A cloud-based management subsystem may be included which is in communication with the communication control module. The communication control module may be configured to track usage of the exercise desk by a plurality of different users, and to implement at least one gamification subsystem. The gamification subsystem may make use of the tracked usages of the users for the purpose of executing a program to reward usage of the exercise device, and may also be configured to report information generated by the gamification subsystem to at least one of the individual or an entity associated with operation of the exercise device. The system may also include an application associated with an information technology (IT) subsystem of the entity associated with operation of the exercise device for facilitating enabling the users to use their respective said personal electronic devices to reserve use of the exercise device during designated time slots.

In still another aspect the present disclosure relates to a method for implementing gamification through an appliance which enables an individual to repeatedly move one or more limbs, and thus acts as an exercise device, while still allowing the individual to perform some other task. The method may comprise providing such an exercise device which is able to be used by the individual to perform movements of one or more limbs which enable the user to achieve a low level aerobic activity while simultaneously performing at least one other non-exercise related task. A communication control module may be used which is able to communicate with a personal electronic device of a user which is located at the exercise device. A management subsystem may be used which is in communication with the communication control module. The management subsystem may be configured to track usage of the exercise device by at least one individual, and to implement at least one gamification program. The gamification subsystem may make use of the tracked usage for the purpose of executing a program to reward usage of the exercise device. The management subsystem may also be used to report information generated by the gamification subsystem to at least one of the individual or an entity associated with operation of the exercise device.

BRIEF DESCRIPTION OF THE DRAWINGS

The drawings described herein are for illustration purposes only and are not intended to limit the scope of the present disclosure in any way.

FIG. 1 is a high level block diagram of a system in accordance with one embodiment of the present disclosure for implementing an appliance which enables repeated movements of one or more limbs of an individual, in this example a treadmill desk, and wherein the treadmill desk includes a desk for supporting a personal electronic device or desktop computer of the user, which is in turn in communication with a cloud-based management system for monitoring activity on the treadmill desk and supplying information to an enterprise associated with the treadmill desk, as well as implementing gamification activities to help promote use and enjoyment of the treadmill desk by workers of the enterprise.

DETAILED DESCRIPTION

The following description is merely exemplary in nature and is not intended to limit the present disclosure, application, or uses. It should be understood that throughout the drawings, corresponding reference numerals indicate like or corresponding parts and features.

Referring to FIG. 1 there is shown a system 10 including a gamified appliance which enables a user to perform a low level aerobic activity (e.g., walking) while performing some other task (e.g., reading emails), and thus the appliance forms an exercise apparatus in accordance with one embodiment of the present disclosure. The system 10 in this example may employ a combination appliance, that is, a combination exercise apparatus, in this example a treadmill 12a, and desk 12b, which collectively will be referred to throughout as a "treadmill desk" 12. The treadmill desk 12 in this example is in communication with a cloud-based management subsystem 14. While the term "treadmill desk" has been used to illustrate the use of a treadmill 12a in connection with a desk 12b, it will be appreciated that other exercise implements could potentially be used. For example a recumbent bicycle or potentially even a stair stepper mechanism could be used in place of a treadmill, and therefore the present disclosure is not limited to only one specific form of exercise-facilitating implement. It is anticipated that a treadmill will be especially desirable as the exercise implement simply because it places the user in an upright position that makes it easy and convenient to work on a keyboard, view a monitor, hand write notes on a note pad if needed, and/or talk on a cell phone or land line telephone while walking. As such, merely for convenience, reference will be made throughout the following discussion to the exercise implement as being a treadmill.

The treadmill desk 12 also includes a communication control module 12c and user controls 12d. A computing device, for example a laptop 12e, may be connected to the communications control module 12c. Alternatively, the user's smartphone may be connected to the communications control module 12c or a desktop computer could be installed at the work desk 12b. The user controls 12d may provide controls for allowing the user to adjust the speed of the treadmill 12a, the incline, an interval program stored on the treadmill 12a, a height of the work desk 12b, or any other feature to enhance user comfort and/or convenience when using the treadmill 12a. The communications control module 12c may be coupled via a suitable cable, for example an HDMI cable, to a larger remote monitor 12f positioned for convenient viewing by the user while walking on the treadmill. Viewing the remote monitor 12f may be preferable to the user when watching webinars, presentations or other events. The communications control module 12c may include a display 12c1 which shows a calendar displaying availability of time slots which are open for reservation by users. The display 12c1 may also be used to display time slots for the day, week or longer which are already booked by users. The display 12c1 may be a touchscreen display or connected external TV/Monitor which allows users to book a time slot for using the treadmill desk 12.

A smartphone 13 may include a suitable smartphone application to enable communication with the management subsystem 14. This enables the user to reserve use of one or more treadmill desks 12 from the user's smartphone. Of course, the smartphone 13 could be substituted for a tablet or even a PC.

The communication control module 12c may be coupled to a router 16 which connects the treadmill desk 12 to an enterprise IT system 18. The router 16 may also be tied in to a wide area network, for example the Internet, to enable the treadmill desk 12 to communicate with the management subsystem 14. An enterprise HR department 20 or HR manager may also be in communication with the enterprise IT system 18. The enterprise IT system 18 may communicate with the management subsystem 14 as well as the communications control module 12c through the router 16. Essentially, the communications control module 12c, enterprise IT system 18 and management subsystem 14 may share any information pertaining to operation of the treadmill desk 12 that may be useful and/or important for the management subsystem 14 or the enterprise IT system 18 to have. The management subsystem 14 may be a third party, cloud-based subsystem operated independently of the enterprise, but under an agreement with the enterprise. The management subsystem 14 controls access to data and resources housed and managed by the subsystem 14.

The management subsystem 14 may include a user portal 14*a* that users of the treadmill desk 12 may access for various purposes. The user portal may be a user portal on a website available on-line or in an intranet environment. Examples of user portal functionality may include providing user access to the past usage history of users (e.g., dates of use, calories burned, miles walked, time spent, points earned, etc.), set preferences (desk height, belt speed, incline, etc.), and to facilitate scheduling future treadmill desk 12 appointments. An "Admin" portal 14*b* allows access to the management subsystem 14 by administrators of the management subsystem. A gamification subsystem 14*c* allows gamification to programs to be implemented and managed by the subsystem 14. The gamification subsystem 14*c* will be described in greater detail in the following paragraphs, but essentially it may contain and/or manage any programs or competitions for encouraging use of the treadmill desk 12 by users in ways that enhance enjoyment and participation among users. Such programs may involve sending out email notices, typically by the management subsystem 14 (but potentially via the enterprise IT system 18) to users informing/reminding them when an activity on the user's calendar (e.g., viewing a webinar, corporate training video, etc.) would lend itself well to performing while using the treadmill desk 12. Another example could be logging minutes spent by different users of the treadmill desk 12 and maintaining scorecards for individuals with the most minutes on the treadmill desk 12. Still another example could be helping to promote favorite charities of employees by managing competitions among users to see who can log the most minutes on the treadmill desk 12 in a given week, month or year, and then allowing the winner to name his/her charity of choice that the enterprise could make a donation to. Still another example of gamification could be having contests among employees of the enterprise for the most minutes, or possibly the most miles, logged on the treadmill desk 12 in a given month or year, and providing additional vacation time to the winner. Other possible competitions could involve tracking the number of calories burned by employees, or possibly by teams of employees, or possibly by employees from various departments of the enterprise, and awarding the winner (or team or department) a prize at the end of the competition. Still another example could involve which employees are the most active and meet their personal goals. For example, an individual who checks in three out of five days in a given week for a session on the treadmill desk 12 may be awarded a point, regardless of how long or how many calories the individual burns in any given session. This arrangement may encourage individuals to at least attempt to start a task or meeting on the treadmill desk 12, which may then result in the individual remaining on the treadmill desk for some reasonable length of time (e.g., possibly 20-30 minutes or longer).

In one embodiment the administrative personnel at the management subsystem 14 may be responsible for managing the gamification of the treadmill desk 12. In other embodiments the administrative personnel may use input from the enterprise it is supporting to set up and implement different gamification-type contests or programs to increase and monitor user participation of the treadmill desk 12. Input may come specifically from the enterprise HR (human resources) department 20 or from other groups/levels/individuals within the enterprise. It will be appreciated that the above examples are but a small number of possible contests/programs that could be implemented via the gamification subsystem 14*c* to promote/track/enhance use and enjoyment of the treadmill desk 12 among users.

In other embodiments the management subsystem 14 may be able to communicate with a specific user's cloud-based personal fitness application. This enables the system 10 to report the minutes logged by a specific user to her/his personal fitness program. The management subsystem 14 may also be in communication with other cloud-based smartphone user applications 24 that the user may wish to employ in connection with her/his operation of the treadmill desk 12.

Still further, the management subsystem 14 may be in communication with a health insurance provider or wellness program 26 associated with the enterprise where the treadmill desk 12 is located. The management subsystem 14 could be used to generate and provide health or activity reports for those individuals who log minutes on the treadmill desk 12. The activities of users could be used by the enterprise insurance provider and/or a wellness program being used by the enterprise to provide premium discounts to those individuals who meet certain use goals on the treadmill desk 12, for example meeting a goal of a certain number of hours logged over the course of a calendar year. If an individual is within a reasonable reach of a participation goal set by the insurance provider, the insurance provider could potentially provide messages to the enterprise IT system 18 through the management subsystem 14, which could be provided to the individual via email notices sent on the enterprise's email system. The email messages may alert the individual on how many additional minutes or hours of activity on the treadmill desk 12 would provide the individual with an award or prize. This may further be used to enhance and encourage participation of the treadmill desk 12.

The enterprise IT system 18 may be based on one or more applications 18*a* from Google, Inc. of Mountain View, Calif., or on the Microsoft Exchange® server management system 18*b* (emails, calendar and contacts management) available from Microsoft Corp. of Redmond, Wash., or any other applications or platforms, and is therefore not constrained to any one type of application or platform. Plug-in applications 18*c* may involve specific applications for enabling users to book or reserve time slots on the treadmill desk 12 or any other applications that enhance the convenience of reserving or using the treadmill desk 12.

The user can schedule the treadmill desk 12 in several different ways. For one, the treadmill desk 12 may be scheduled as a meeting resource similar to the way that a conference room or projector can be added to a meeting appointment. This is done using the normal mechanism in the Microsoft Outlook® email application. (This runs in 18*a*/18*b*). Another way to schedule is by including treadmill@workdesk.com (example email address) in the meeting invitation created in the Microsoft Outlook® email application or using Google applications. The management subsystem 14 receives the email and based on the user that sent the email, the subsystem 14 matches her preferred (and available) treadmill desks to the meeting time. The management subsystem 14 may then respond that the treadmill desk 12 will attend the meeting along with the specific treadmill desk 12 (assuming a plurality of treadmill desks are available for use at the enterprise) that the user should use. If there is no treadmill desk 12 available at the meeting time, an email is sent to the user indicating so and offering other available times and/or treadmill desks that are available but not on her/his preferred list. This scenario may be executed in the management subsystem 14.

Still another way to schedule the treadmill desk 12 will be by using the management subsystem 14, having been previously granted access to a user's calendar (18a/18b), to periodically scan the user's calendar. Scanning the user's calendar may be for keywords that indicate that an appointment may be conducive to working at a treadmill. If a match is found an email is then sent to the user offering to add the treadmill desk 12 to the appointments.

Still another scheduling method may involve having the management subsystem 14 periodically review a user's usage history. When the management subsystem 14 finds that the user hasn't been on the treadmill desk 12 recently, the management subsystem 14 may send a reminder email to get up and get moving with upcoming treadmill desk availability.

Still another scheduling method may be by adding custom code that can be installed on the corporate calendar servers (18a/18b). In this manner the user interface for the appointment creation function is modified to include a checkbox for scheduling a treadmill desk 12 into the appointment. This can potentially work in several different ways: 1) ticking the checkbox has the same effect as including treadmill@workdesk.com in the appointment invitation as described above; and 2) the checkbox only appears if one or more of the users preferred treadmill desks are available. The second option immediately above requires communication between the enterprise IT system 18 and the management subsystem 14.

A number of options and/or enhancements may also be included with the system 10. For example, a scale may be installed under the treadmill belt of the treadmill desk 12 to measure the weight of the user on the treadmill desk. The system 10 could be modified to show utilization time of the treadmill. Specifically, showing the amount of time remaining for a scheduled user, and if there is open time, using the management subsystem 14 to proactively find new users to automatically fill all or part of a given time slot where the treadmill desk 12 is free for use. The management subsystem 14 could be used to notify users (e.g., by email messages) that an increased number of points or other reward incentives is currently available to help incentivize users to fill unused treadmill desk 12 time slots. The management subsystem 14 could also incorporate push notifications on the smartphone 13 from a given treadmill desk 12, so the treadmill desk 12 notifies one or more individuals (potentially a group of individuals) that a given treadmill desk 12 is free to use at one or more specific time slots. The management subsystem 14 could also be used to help facilitate user calendar automation by booking a treadmill desk 12 based on specific keywords (e.g., GoToMeeting™ on-line meeting, WeBex™ on-line meeting). Thus, whenever the management subsystem 14 sees a certain keyword on the user's calendar, the management system can proactively take action in an effort to fill up available use slots for one or more of the treadmill desks 12.

If the user's email/calendar system enables selecting the treadmill desk 12, then the user could add it to the meeting invitee list. An additional point regarding emails is that the email that is added for the treadmill desk 12 is not unique. Any user may just add a generic email (e.g. desk@workdesk.com) and the system 10 may automatically book a treadmill desk 12 based on the user's email (i.e., location where the email is coming from) and a database lookup of treadmill desks 12 that are available and in an appropriate location. These features are expected to make it especially easy for users to reserve time slots on one or more of the treadmill desks 12.

Still further, the system 10 may use the user's cellular phone number to notify the user with a text message that a certain activity on the user's calendar would lend itself well to performing while using the treadmill desk 12. The system 10 could just as easily alert a user that a different user has cancelled an appointment slot on the treadmill desk 12 and the treadmill desk is now available for immediate use. Accordingly, email, SMS and push notification are all technologies that may be implemented with the system 10 to maximize the opportunity for individuals to make use of the treadmill desk 12.

The system 10 enables users to gain valuable cardiovascular exercise during those periods of the day where they would otherwise be carrying out a task seated in a chair, but where the task could just as easily be carried out while walking at a comfortable/leisurely pace on a treadmill. A wide variety of tasks such as webinars, employee training, answering voicemail messages, responding to emails and other activities can easily be carried out while walking at a comfortable pace, and without causing such exertion that the individual would begin to perspire. The system 10 provides the valuable advantage that the individual may obtain cardiovascular exercise during normal working hours, which means that those times outside of an individual's working hours would be free for family or other activities. Use of the system 10 may potentially enable some individuals to forego one or more trips per week or month to a health club, where the activity at the health club would be the same as walking on a treadmill, which would further provide more leisure and/or family time to the individual. The overall health of employees of the enterprise may be improved, thus helping to reduce health related costs for the enterprise.

While various embodiments have been described, those skilled in the art will recognize modifications or variations which might be made without departing from the present disclosure. The examples illustrate the various embodiments and are not intended to limit the present disclosure. Therefore, the description and any claims should be interpreted liberally with only such limitation as is necessary in view of the pertinent prior art.

What is claimed is:

1. An exercise system comprising:
    an appliance which allows movement of one of more limbs of a user, which enables a low level aerobic activity to be achieved by an individual, and thus acts as an exercise device for the individual while the individual is simultaneously performing other non-exercise related tasks;
    a communication control module able to communicate with a personal electronic device located at the exercise device;
    a management subsystem in communication with the communication control module configured to:
        track accumulated usage of the exercise device by the individual, as well as accumulated exercise device usage accumulated by other individuals occurring on the appliance;
        implement at least one gamification program, the gamification program making use of the tracked accumulated usage of the individual and the other individuals for the purpose of executing a program to reward usage of the exercise device to a specific individual who first meets a usage threshold within a given time period; and to report information generated by the gamification program to at least one of the individual or an entity associated with operation of the exercise device.

2. The system of claim 1, wherein the communication module is configured to communicate with an information technology (IT) subsystem of the entity associated with the operation of the exercise device.

3. The system of claim 2, further comprising an application installed on an electronic device associated with the IT subsystem of the entity to enable at least one of an email system or a calendar system to be used in connection with enabling the individual to reserve a time slot for using the exercise device.

4. The system of claim 2, further comprising an application installed on an electronic device associated with the IT subsystem of the entity to enable the IT subsystem of the entity to be used to suggest, through an email message to the individual, at least one of:
 when usage of the exercise device should be considered;
 when the individual has accumulated an amount of usage time on the exercise device to qualify for an award; or
 when an upcoming event on the individual's calendar could be performed while using the exercise device.

5. The system of claim 4, wherein the user is able to use the personal electronic device located at the exercise device to communicate with the entity associated with operation of the exercise desk to respond to an email suggesting use of the exercise device during an upcoming event, and to reserve the exercise device for use at a time in accordance with the upcoming event.

6. The system of claim 1, wherein the management subsystem is able to communicate with a Cloud-based fitness application associated with the individual.

7. The system of claim 1, further comprising a user control subsystem for allowing the user to adjust one or more features of the exercise device.

8. The system of claim 1, wherein the exercise device comprises a treadmill.

9. The system of claim 1, wherein the management subsystem is in communication with one of:
 a cloud-based insurance provider;
 a cloud-based wellness program; or
 a personal fitness application of the individual.

10. The system of claim 1, wherein the management subsystem includes at least one of:
 a user portal at which the individual using the exercise desk can log in; or
 an administrative portal which enables access to the management subsystem by the entity associated with operation of the exercise device.

11. The system of claim 1, wherein the management subsystem is able to communicate with a human resources department of the entity associated with operation of the exercise device.

12. The system of claim 1, wherein the system includes a plurality of exercise devices, and the management tracks the usage of each one of the plurality of exercise devices to enable a plurality of individuals to track their respective usage of one or more of the plurality of exercise devices over a given time period.

13. An exercise system comprising:
 a plurality of appliances which allow for movement of one of more limbs of users, which enable a low level aerobic activity to be achieved by individuals, and thus act as a plurality of exercise devices for the individuals while the individuals are simultaneously performing other non-exercise related tasks;
 a communication control module able to communicate with a plurality of personal electronic devices located at the exercise devices;
 an information technology (IT) subsystem of an entity associated with the operation of the exercise devices which informs each of the individuals, via an unsolicited electronic message to the user's PED, as to a status of availability of one or more of the exercise devices;
 a management subsystem in communication with the communication control module configured to:
 track a parameter related to an accumulated usage of one or more of the exercise devices by each one of the individuals;
 implement at least one gamification program, the gamification program making use of the tracked parameter for the purpose of executing a program to reward usage of the exercise device to a specific individual with a maximum value for the tracked parameter within a given time frame; and
 to report information generated by the gamification program to at least one of the individual or an entity associated with operation of the exercise device.

* * * * *